(12) United States Patent
Matsumoto et al.

(10) Patent No.: US 7,740,577 B2
(45) Date of Patent: Jun. 22, 2010

(54) REPAIRING METHOD FOR ENDOSCOPE AND ENDOSCOPE INFRARED HEATING SYSTEM

(75) Inventors: Jun Matsumoto, Tokyo (JP); Tatsuya Shimada, Tokyo (JP); Toshiyuki Nihei, Tokyo (JP)

(73) Assignee: Olympus Corporation (JP)

( * ) Notice: Subject to any disclaimer, the term of this patent is extended or adjusted under 35 U.S.C. 154(b) by 647 days.

(21) Appl. No.: 11/056,972

(22) Filed: Feb. 11, 2005

(65) Prior Publication Data

US 2005/0203337 A1    Sep. 15, 2005

(30) Foreign Application Priority Data

Feb. 13, 2004    (JP)    ............................. 2004-036662
Oct. 21, 2004    (JP)    ............................. 2004-306910

(51) Int. Cl.
*A61B 1/00*    (2006.01)
*A61M 25/00*    (2006.01)

(52) U.S. Cl. ...................................... 600/101; 604/524

(58) Field of Classification Search ................ 432/121, 432/122, 147, 184; 264/614, 36.1–36.22, 264/140; 427/340; 53/469; 250/495.1, 504 R; 219/130.21, 411, 711, 553; 392/540, 343, 392/346, 418; 600/101, 102, 920, 133; 604/537
See application file for complete search history.

(56) References Cited

U.S. PATENT DOCUMENTS

| | | | | |
|---|---|---|---|---|
| 4,179,529 A | * | 12/1979 | Vetter | .......................... 427/513 |
| 4,426,570 A | * | 1/1984 | Hikino et al. | ................ 219/553 |
| 4,462,307 A | * | 7/1984 | Wells | ........................... 99/386 |
| 4,464,563 A | * | 8/1984 | Jewett | ......................... 392/470 |
| 4,495,134 A | * | 1/1985 | Ouchi et al. | ................. 264/516 |
| 4,860,732 A | * | 8/1989 | Hasegawa et al. | ............ 600/109 |
| 4,940,307 A | * | 7/1990 | Aberson et al. | ................ 385/98 |
| 5,259,999 A | * | 11/1993 | Iwakiri et al. | .............. 264/1.36 |
| 5,569,221 A | * | 10/1996 | Houser et al. | ................ 604/524 |
| 5,859,412 A | * | 1/1999 | Yagi | ........................... 219/704 |
| 5,885,207 A | * | 3/1999 | Iwasaka | ...................... 600/139 |
| 6,100,339 A | * | 8/2000 | Watanabe et al. | ............ 525/216 |
| 6,627,116 B1 | * | 9/2003 | Suda et al. | ................... 252/502 |
| 6,929,601 B2 | * | 8/2005 | Nakao | ......................... 600/121 |
| 2003/0105453 A1 | * | 6/2003 | Stewart et al. | ............... 604/537 |

FOREIGN PATENT DOCUMENTS

JP    6-70877    3/1994
JP    2002-135934    5/2002

OTHER PUBLICATIONS

English translation of Japanese Office Action dated May 29, 2008 relating to Japanese Patent Application No. 2004-306910.

* cited by examiner

*Primary Examiner*—Linda C Dvorak
*Assistant Examiner*—Alireza Nia
(74) *Attorney, Agent, or Firm*—Ostrolenk Faber LLP

(57) ABSTRACT

A repairing method for an endoscope includes inserting into a cylindrical heating element a repair part of at least one endoscope having a resin material applied on an outer peripheral surface of the endoscope, causing the heating element to generate heat by supplying power to the heating element in order to radiate infrared rays from the heating element toward the center of the cylinder, and drying/hardening the resin material in the repair part by using the infrared rays radiated from the heating element.

27 Claims, 5 Drawing Sheets

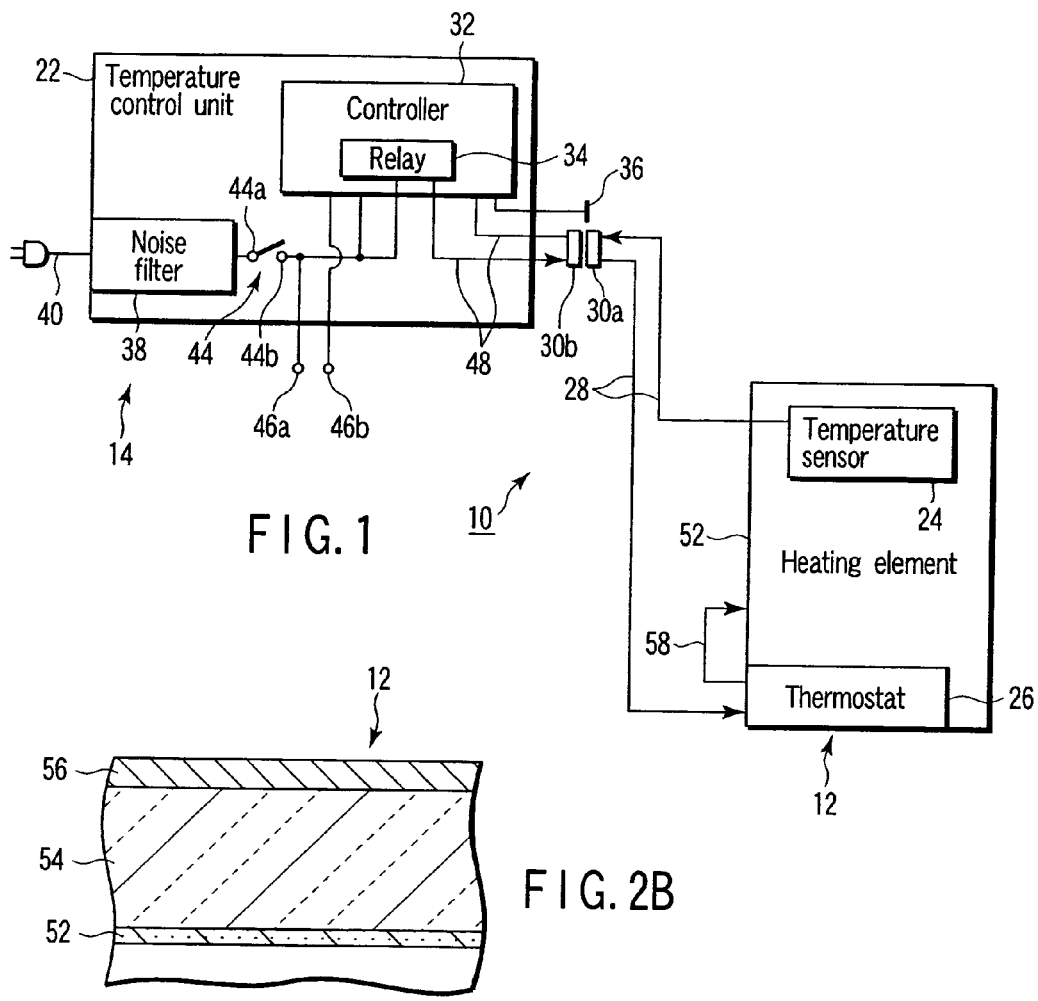
FIG. 1
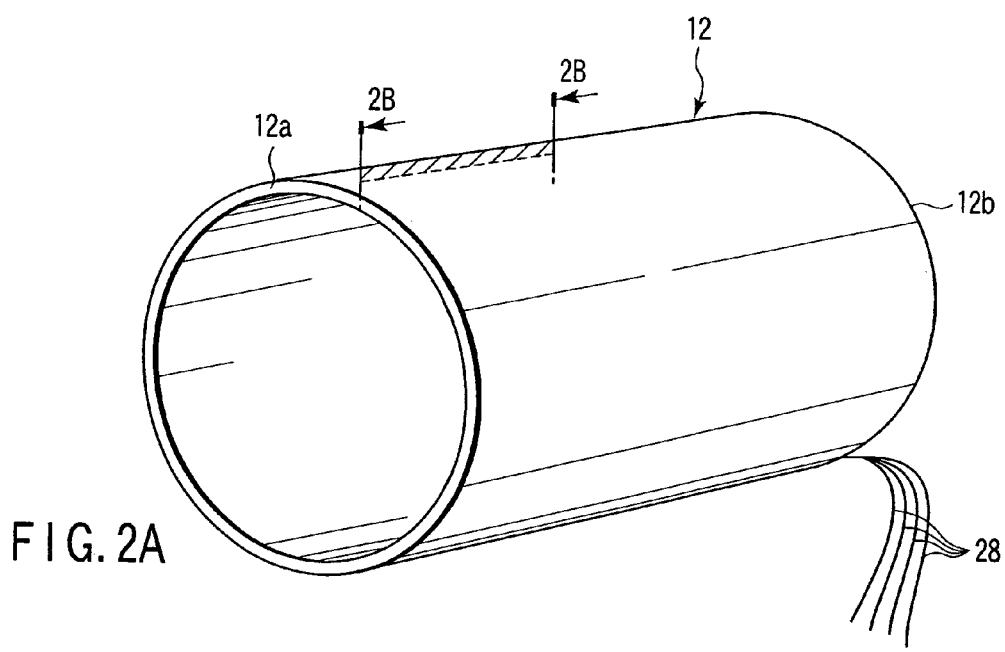
FIG. 2B
FIG. 2A

REPAIRING METHOD FOR ENDOSCOPE AND ENDOSCOPE INFRARED HEATING SYSTEM

CROSS-REFERENCE TO RELATED APPLICATIONS

This application is based upon and claims the benefit of priority from prior Japanese Patent Applications No. 2004-036662, filed Feb. 13, 2004; and No. 2004-306910, filed Oct. 21, 2004, the entire contents of both of which are incorporated herein by reference.

BACKGROUND OF THE INVENTION

1. Field of the Invention

The present invention relates to a repairing method for an endoscope and an endoscope infrared heating system which perform adhesion repair or coat repair of an integument or a channel tube of an endoscope which is used in, e.g., a medical field.

2. Description of the Related Art

In general, a medical endoscope has an insertion section in which an inflectional portion which is bent as a result of manipulation by an operator is provided at an end portion of a flexible tube. A hard end portion having an objective optical system is arranged at an end portion of the inflectional portion of the insertion section. This objective optical system is optically connected with an image guide extending to a base end portion side of the insertion section through the inside of the inflectional portion. Therefore, when the inflectional portion is bent in a state that the insertion section is being inserted to a desired position in a body cavity, an image of a desired part in the body can be obtained by using the objective optical system.

The obtained image data is taken into an ocular portion by using the image guide. Treatment of a diseased part is performed by inserting an appropriate treatment instrument into a channel of the insertion section while confirming the diseased part based on this image data.

After inspection or treatment using such an endoscope, cleansing, sterilization and disinfection of the endoscope or its attachments must be performed in order to avoid infectious diseases. After such processing, the endoscope is reused.

BRIEF SUMMARY OF THE INVENTION

According to one aspect of the present invention, there is provided a repairing method for an endoscope including:

inserting a repair part of at least one endoscope having a resin material applied to an outer peripheral surface thereof into a cylindrical heating element;

causing the heating element to generate heat by supplying a power to the heating element in order to radiate infrared rays from the heating element toward the center of the cylinder; and drying/hardening the resin material at the repair part by using the infrared rays radiated from the heating element.

Advantages of the invention will be set forth in the description which follows, and in part will be obvious from the description, or may be learned by practice of the invention.

Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram showing a control system of an endoscope infrared heating system according to a first embodiment;

FIG. 2A is a schematic perspective view showing a drying furnace in the endoscope infrared heating system according to the first embodiment;

FIG. 2B is a cross-sectional view taken along the line 2B-2B in FIG. 2A, showing the drying furnace in the endoscope infrared heating system according to the first embodiment;

DETAILED DESCRIPTION OF THE INVENTION

A best mode for embodying the present invention will now be described hereinafter with reference to the accompanying drawings.

A first embodiment will be explained with reference to FIGS. 1 to 7B.

Figure 3:
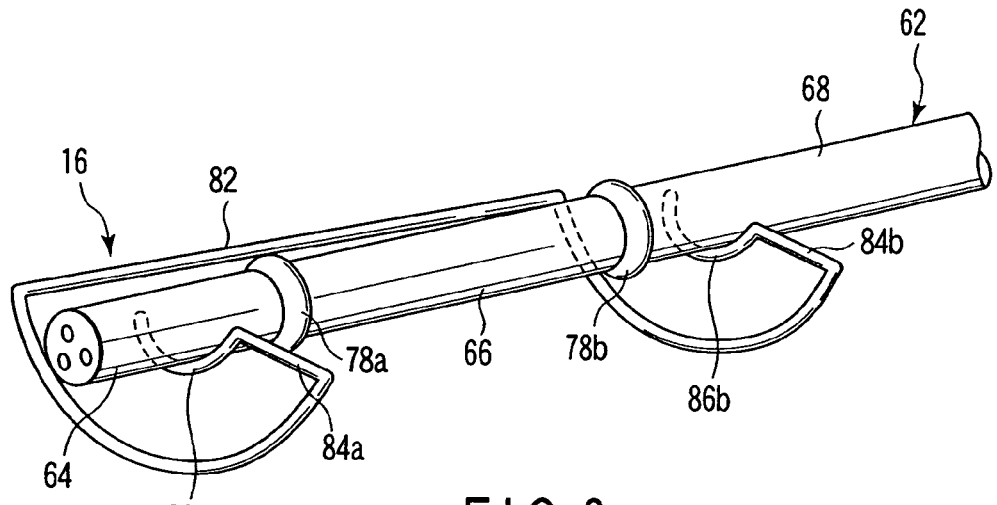
FIG. 3 is a schematic perspective view showing a state in which an insertion section of an endoscope is arranged in an endoscope holding jig in the endoscope infrared heating system according to the first embodiment.

As shown in FIG. 1, an endoscope infrared heating system (an endoscope infrared heating apparatus) 10 according to this embodiment includes an infrared drying furnace 12 (see FIG. 2A), a temperature control unit 14, and an endoscope holding jig 16 (see FIG. 3). The endoscope holding jig 16 is used to hold the vicinity of a repair/mending part of an insertion section 62 or the like of a later-described endoscope (see FIG. 4A). The infrared drying furnace 12 is used to radiate an infrared ray and apply heat to the insertion section 62 or the like of the endoscope held by the endoscope holding jig 16. The temperature control unit 14 is used to detect a temperature at a predetermined position in the drying furnace 12, adjust a power supplied to the drying furnace 12 based on the detected temperature and control the inside of the drying furnace 12 at an appropriate temperature.

As the infrared rays radiated in the drying furnace 12, it is possible to use one of near-infrared rays, mid-infrared rays and far-infrared rays. In particular, far-infrared rays in a given fixed wavelength range can be readily absorbed into a material and have characteristics that the thermal effect is high, and hence using far-infrared rays is preferable.

A structure of the temperature control unit 14 will now be described with reference to FIG. 1.

The temperature control unit 14 includes a main body (a case) 22, a temperature sensor (a temperature detection portion) 24 formed of, e.g., a thermocouple, and a thermostat 26. The temperature sensor 24 and the thermostat 26 are arranged in the infrared drying furnace 12. Cords 28 extend from the temperature sensor 24 and the thermostat 26. A first connection connector 30a is attached at end portions of these cords 28. That is, the first connection connector 30a is electrically connected with an output end of the temperature sensor 24 and an input end of the thermostat 26.

The main body 22 includes a controller 32, a relay 34, an emergency stop switch 36, a noise filter 38 and a power supply cord 40.

A switch 44 which cooperates with an operation of a non-illustrated operation button provided to the main body 22 is provided between the noise filter 38 and the controller 32. The switch 44 includes a movable contact point 44a connected with the noise filter 38 and a fixed contact point 44b connected with one end (an input end) of the relay 34 and the controller 32. A first display lamp 46a composed of an LED is connected with the controller 32. The first display lamp 46a emits, e.g., a green light when the movable contact point 44a of the switch 44 is electrically connected with the fixed contact point 44b of the same. Therefore, when the movable contact point 44a of the switch 44 is electrically connected with the fixed contact point 44b of the same in a state that the power supply cord 40 is connected with an external power supply (not shown), power from the external power supply is supplied to the controller 32 through the power supply cord 40, the noise filter 38 and the switch 44, and the first display lamp 46a emits light.

A second display lamp 46b composed of an LED is further connected with the controller 32. The second display lamp 46b emits, e.g., red light when the temperature in the infrared drying furnace 12 detected by the temperature sensor 24 reaches a temperature set in the controller 32 with an error range of several percent.

The relay 34 and the controller 32 are electrically connected with each other. The relay 34 is controlled by the controller 32. Cords 48 extend from the other end (an output end) of the relay 34 and an output/input end of the controller 32. A second connection connector 30b is attached at end portions of these cords 48.

The second connection connector 30b can be separated from/coupled with, i.e., detachably attached to the first connection connector 30a. When the first and second connection connectors 30a and 30b are coupled with each other, the controller 32 is electrically connected with the temperature sensor 24, and the other end of the relay 34 is electrically connected with the thermostat 26.

Therefore, the controller 32 uses the thermostat 26 to control a maximum temperature in the drying furnace 12 set by a user based on data from the temperature sensor 24 which has detected the temperature in the drying furnace 12.

The emergency stop switch 36 is electrically connected with the controller 32. The emergency stop switch 36 forcibly stops supply of a power to the thermostat 26 through the relay 36 when pressed, for example.

A structure of the infrared ray drying furnace 12 will now be described with reference to FIGS. 2A and 2B.

As shown in FIG. 2A, the infrared drying furnace 12 is formed into a substantially cylindrical shape having first and second opening portions 12a and 12b. As shown in FIG. 2B, the infrared drying furnace 12 includes a heating element 52 arranged on an inner peripheral surface of the cylinder, a heat insulating material 54 which covers an outer periphery of the heating element 52, and a holding frame 56 which covers the outer periphery of the heat insulating material 54 and maintains shapes of the heating element 52 and the heat insulating material 54. That is, the infrared drying furnace 12 is formed into a cylindrical shape in a state that the heating element 52, the heat insulating material 54 and the holding frame 56 are sequentially superimposed from the inner peripheral surface toward the outer peripheral surface.

Although not shown, the heating element 52 includes a heating member (an electroconductive resistor) formed into, e.g., a fabric sheet shape with, e.g., paper and carbon fibers are mixed therein, a pair of terminals attached to the heating member in order to supply power to the heating member, and a heat-resisting resin material formed into a sheet shape to hold the heating member therein. Since the heating member is formed in a fabric state, the probability of a breaking failure can be reduced.

Each terminal is electrically connected with the thermostat 26 through a lead 58 (see FIG. 1). That is, the thermostat 26 is electrically connected with the heating element 52. The thermostat 26 stops supply of power to the heating element 52 from the thermostat 26 through the lead 58, or adjusts the supply quantity of power to maintain the temperature in the drying furnace 12 at a desired temperature when the temperature in the drying furnace 12 detected by the temperature sensor 24 reaches a predetermined temperature, e.g., 120 degrees, thereby avoiding an increase in temperature.

The heating member of this heating element 52 is arranged in a state that it is held by the heat-resisting resin material which transmits infrared rays therethrough and an inner part thereof is thereby depressurized (a substantially vacuum state). As the heat-resisting resin material, a polymeric material such as glass epoxy is used. The thickness of the thus formed heating element 52 is approximately 0.5 mm.

The heating element 52 has a surface heating structure which is the excellent thermal conduction efficiency to the ambit (atmosphere), and which substantially evenly radiates far-infrared rays which are hardly affected by an air stream or the like toward an axial center of the drying furnace 12. If the heating element 52 has the surface heating structure, it is possible maintain a distance from the heating element 52 constant by the structure rather than a point heating structure or a line heating structure.

As the heat insulating material 54, there is used a material which is light and has a high heat-resisting effect, e.g., polyethylene foam or polyurethane foam. The thickness of the heat insulating material 54 is approximately 5 mm. As to the holding frame 56, a metal sheet material of, e.g., aluminium is formed into a cylindrical shape. The thickness of this holding frame 56 is approximately 1 mm.

The temperature sensor 24 shown in FIG. 1 is arranged in the drying furnace 12 so that the temperature in the vicinity of, e.g., the center of the drying furnace 12 can be measured. The temperature sensor 24 transmits to the controller 32 detected temperature data through the cords 28 (see FIG. 2A), the first and second connection connectors 30a and 30b and the cords 48 mentioned above.

The entire length and diameter of the cylindrical drying furnace 12 in which the temperature sensor 24 or the thermostat 26 is arranged in this manner are formed into a size which facilitates being carried by a user or the like. Therefore, when the drying furnace 12 has the above-described structure, it has a very light weight and can be readily carried.

Figure 4A:
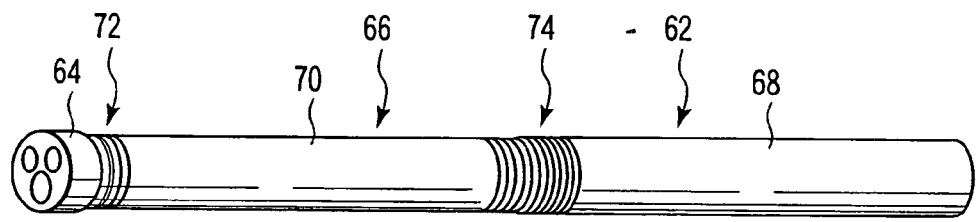
FIG. 4A is a schematic perspective view of an endoscope repaired by the endoscope infrared heating system according to the first embodiment, showing a state in which first and second spool portions are formed to the insertion section.

As shown in FIG. 4A, an endoscope includes an elongated insertion section 62 and a non-illustrated operation section provided to a proximal end portion of the insertion section 62. The insertion section 62 has on the same axis an end hard portion 64, a inflectional portion 66 provided to a proximal end portion of the end hard portion 64, and a flexible tube 68 provided to a proximal end portion of the inflectional portion 66. A proximal end portion of the flexible tube 68 is fixed to the operation portion.

Figure 4B:
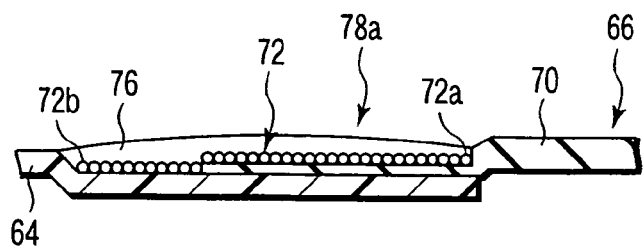
FIG. 4B is a schematic cross-sectional view of the endoscope repaired by the endoscope infrared heating system according to the first embodiment, showing an end portion of the insertion section including the first spool portion.

A first spool portion 72 is formed at a distal end portion (the proximal end portion of the end hard portion 64) of an integument 70 of the inflectional portion 66. A second spool portion 74 is formed at a proximal end portion (the distal end portion of the flexible tube 68) of the integument 70 of the inflectional portion 66. As shown in FIG. 4B, an adhesive application portion 76 to which an adhesive is applied is formed to the first spool portion 72. Although not shown, the same portion is formed to the second spool portion 74.

The structure of the endoscope holding jig 16 will now be described with reference to FIG. 3.

As shown in FIG. 3, the jig 16 integrally includes a mount portion 82 which is mounted on an inner peripheral surface of the heating element 52 of the drying furnace 12 and two holding portions 84a and 84b which hold a part of the insertion section 62 of the endoscope. Since the endoscope holding jig 16 requires the heat resisting properties, e.g., a metal wire rod is bent and formed in the infrared drying furnace 12 in such a manner that it can be accommodated therein.

Concave portions 86a and 86b are respectively formed to the holding portions 84a and 84b in order to hold a part of the insertion section 62 of one endoscope. It is to be noted that these concave portions 86a and 86b have the elasticity may be elastically deformed and capable of holding a part of the insertion section 62 while avoiding movement of the insertion section 62 in the axial direction or rotation of the same around the axis when the part of the insertion section 62 is arranged therein.

The mount portion 82 is formed into a semi-circular shape which is mounted along the inner peripheral surface of the heating element 52 of the drying furnace 12.

The distance between the respective holding portions 84a and 84b is formed slightly longer than a length between the distal and proximal ends of the inflectional portion 66. Therefore, a repair part of the insertion section 62 is arranged and held on the inner side of the holding portions 84a and 84b facing each other in the jig 16. When the jig 16 is accommodated in the drying furnace 12, the holding portions 84a and 84b are arranged on the substantially central axis of the drying furnace 12.

Description will now be given as to an operation which replaces the integument 70 (see FIG. 4B) of the inflectional portion 66 of the insertion section 62 of the endoscope with a new integument 70 as a first operation of the endoscope infrared heating system 10 according to the embodiment.

An adhesive which is applied and hardened at the distal end portion (the proximal end portion of the distal end hard portion 64) of the inflectional portion 66 and the proximal end portion (the distal end portion of the flexible tube 68) of the inflectional portion 66 of the insertion section 62 of the endoscope to be repaired is removed. Threads wound around the first and second spool portions 72 and 74 (see FIG. 4A) formed at the end portion and the proximal end portion of the inflectional portion 66 are respectively removed. The integument 70 arranged on the outer peripheral surface of the inflectional portion 66 is removed.

As shown in FIG. 4B, the outer periphery of the inflectional portion 66 is covered with a new integument 70. A thread is closely wound on the outer side of the end portion of the integument 70 of the inflectional portion 66, and the end portion of the integument 70 is fixed to the proximal end portion of the distal end hard portion 64. In this manner, the first spool portion 72 shown in FIG. 4A is formed.

The thread forming the first spool portion 72 is started to be wound from a winding start portion 72a at the distal end of the integument 70, and terminated at a winding end portion 72b of the concave portion at the proximal end portion of the distal end hard portion 64. An end portion of the thread is fixed under the thread wound between the winding start portion 72a and the winding end portion 72b.

Likewise, a thread is closely wound on the outer side of the proximal end portion (the proximal end portion of the integument 70) of the inflectional portion 66, and the proximal end portion of the integument 70 is fixed at the distal end portion of the flexible portion 68. In this manner, the second spool portion 74 shown in FIG. 4A is formed.

As shown in FIG. 4B, the adhesive application portion 76 to which, e.g., an epoxy-based 2 liquid thermosetting adhesive is applied is formed from the outer side of these first and second spool portions 72 and 74. As to the application portion 76, an adhesive is applied to completely cover the first and second spool portions 72 and 74 in order to achieve perfect water tightness of the first and second spool portions 72 and 74 at the end of hardening. In this manner, first and second repair portions 78a and 78b are formed.

As shown in FIG. 3, the distal end portion side and the proximal end side of the inflectional portion 66 of the insertion section 62 in this state are arranged in the holding portions 84a and 84b of the endoscope holding jig 16. At this time, the insertion section 62 is inserted into a hole formed in a central portion of a closing plate (not shown) which closes a second opening portion 12b of the drying furnace 12.

Figure 5:
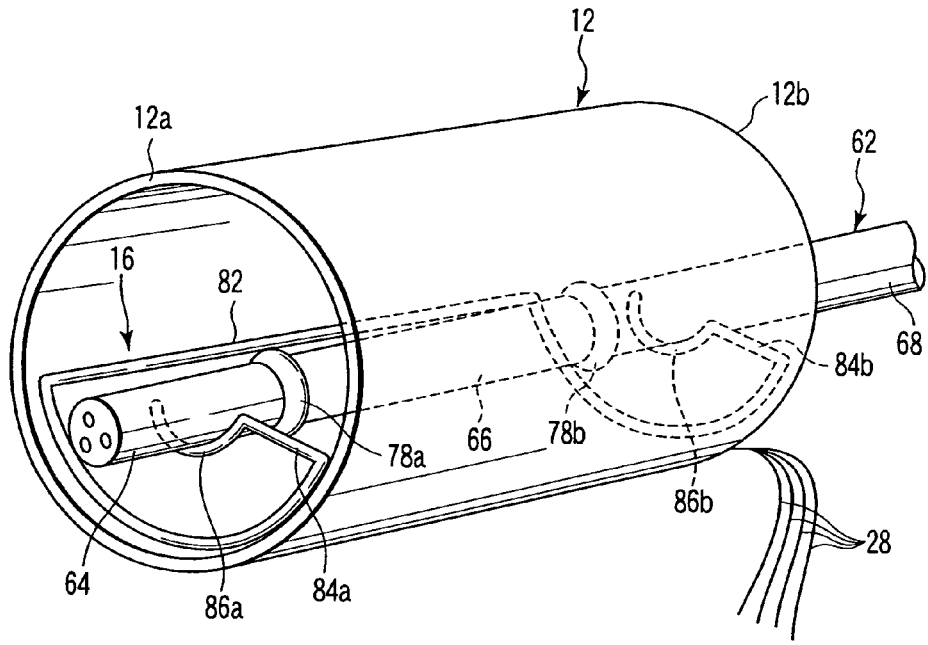
FIG. 5 is a schematic perspective view showing a state in which the insertion section of the endoscope is arranged in the endoscope infrared heating system according to the first embodiment.

As shown in FIG. 5, the jig 16 having the first and second repair portions 78a and 78b of the insertion section 62 of the endoscope being arranged between the holding portions 84a and 84b is arranged in the drying furnace 12 which is horizontally arranged by a stand (not shown). At this moment, the holding portions 84a and 84b are placed on the substantially central axis of the drying furnace 12. That is, the central axis of the first and second repair portions 78a and 78b is placed on the substantially central axis of the drying furnace 12. In this state, the first and second opening portions 12a and 12b are closed by using the closing plates (not shown) having the heat insulating properties. At this time, the second opening portion 12b is closed by sliding the closing plate having the insertion section 62 inserted therethrough along the insertion section 62.

Then, the drying furnace 12 is electrically connected with the temperature control unit 14 by the first and second connection connectors 30a and 30b. Specifically, the first connection connector 30a of the heating element 52 of the drying furnace 12 is coupled with the second connection connector 30b of the main body 22 of the temperature control unit 14.

A drying/hardening program, e.g., the maximum temperature obtained when the temperature in the drying furnace 12 is increased by operating the controller 32 of the temperature control unit 14, the time required to dry/harden the adhesive in the application portion 76 and others are set. The temperature is the temperature obtained by the temperature sensor 24. In this example, the maximum temperature in the drying furnace 12 is set to, e.g., 80 degrees. That is, the set temperature of the thermostat 26 is determined as 80 degrees. The time required to harden the adhesive in the application portion 76 is determined as 20 minutes in a state wherein the temperature of 80 degrees is maintained. Of course, an error of several percent of the time or the temperature can be allowed.

The switch 44 is turned on by manipulating the non-illustrated operation switch provided on the main body 22. Power from the external power supply is supplied to the heating element 52 through the power supply cord 40, the nozzle filter 38, the relay 34 and the thermostat 26, and the first display lamp 46a is turned on.

The heating element 52 generates heat by supply of power, and radiates far-infrared rays toward the central axis in the drying furnace 12. Therefore, the temperature in the drying furnace 12 is increased. Since the heating element 52 has a surface heating structure, it evenly heats the application portion 76 at the distal and proximal end portions of the inflectional portion 66.

The controller 32 sequentially acquires detection signals from the temperature sensor 24 at appropriate time intervals or the like. The controller 32 outputs the temperature data acquired by the temperature sensor 24 to the thermostat 26. The thermostat 26 adjusts the power to be input to the heating element 52 based on the temperature data. If the temperature in the temperature data does not reach 80 degrees, supply of power to the heating element 52 is allowed. If the temperature in the temperature data has reached 80 degrees, the supply quantity of power to the heating element 52 is adjusted in such a manner that the temperature data maintains a temperature in the vicinity of 80 degrees.

Figure 6:
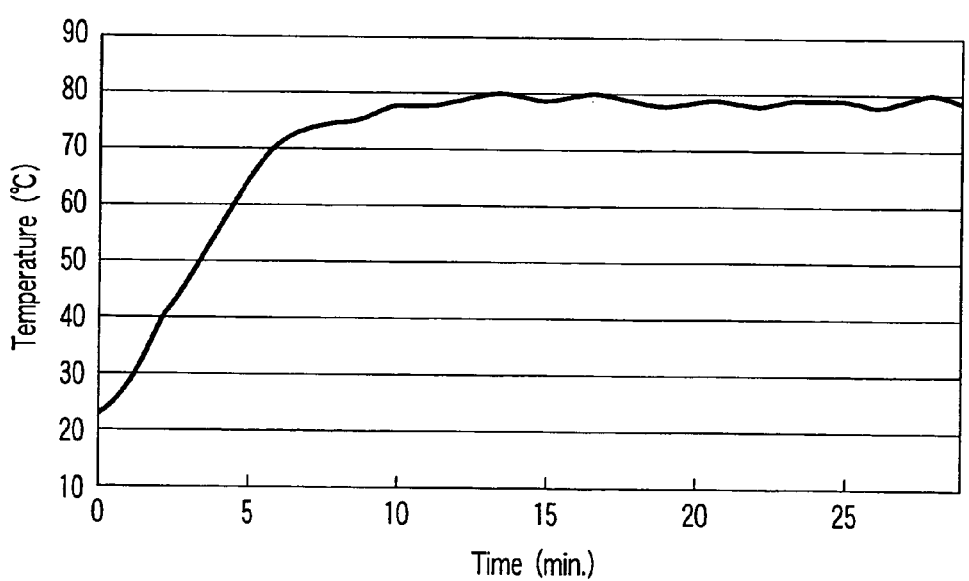
FIG. 6 is a graph showing temperature change with respect to time required to dry and harden a repair part of the insertion section in a state that the insertion section of the endoscope is arranged in the drying furnace in the endoscope infrared heating system according to the first embodiment and the temperature in the drying furnace is controlled.

As shown in FIG. 6, when the heating element 52 having the surface heating structure according to the embodiment is used, the detected temperature data obtained by the temperature sensor 24 reaches approximately 80 degrees from an ordinary temperature in approximately six to seven minutes. When the detected temperature data reaches a desired temperature (approximately 80 degrees) with an error range of several percent, the second display lamp 46b is turned on.

When the temperature has once reached approximately 80 degrees by the effect of the thermostat 26, this temperature (approximately 80 degrees) is then maintained. That is, the thermostat 26 avoids excessive heating in the drying furnace 12. The controller 32 controls the thermostat 26 in order to maintain 80 degrees for approximately 20 minutes. The epoxy-based adhesive is dried and hardened in this manner.

After maintaining 80 degrees for approximately 20 minutes, the controller 32 automatically interrupts supply of the power to the heating element 52. That is, after the elapse of a predetermined time required to harden the adhesive, the controller 32 releases the switch 44 in the main body 22, and stops the supply of power to the heating element 52. Therefore, the inside of the drying furnace 12 is gradually cooled down.

In the far-infrared radiation state with the power being supplied to the heating element 52, when radiation by the heating element 52 is forcibly stopped for example, the emergency stop switch 36 is pressed. A signal obtained by pressing this emergency stop button 36 is input to the controller 32. The controller 32 controls the thermostat 26, and interrupts the supply of power to the heating element 52. Therefore, radiation of far-infrared rays by the heating element 52 is stopped.

After termination of hardening of the adhesive in the application portion 76 of the first and second repair portions 78a and 78b, the first and second connection connectors 30a and 30b are disconnected from each other. After confirming that the inside of the drying furnace 12 is sufficiently cooled, the drying furnace 12 or the temperature control unit 14 is carried to each desired place.

It is to be noted that the drying furnace 12 can be carried to a desired place before the inside of the drying furnace 12 is sufficiently cooled. It is preferable that this portage is possible only when the holding frame 56 is maintained at a temperature enabling portage by hands.

In or after gradual cooling, the insertion section 62 only or together with the jig 16 is removed from the drying furnace 12. Water tightness or the like of the first and second repair portions 78a and 78b of the insertion section 62 of the endoscope is checked, and the endoscope is cleansed, sanitized and disinfected so that it can be reused.

Although description has been given as to a use of the epoxy-based 2 liquid thermosetting adhesive as the adhesive in the application portion 76 in connection with the first operation, an epoxy-based 1 liquid thermosetting adhesive or any other thermosetting adhesive may be used.

Although description has been given as to drying and hardening the adhesive in the application portion 76 in connection with the first operation, drying can be likewise carried out when, e.g., a coat layer which is formed on an outermost layer of the flexible tube 68 or the like of the insertion section 62 and protects the flexible tube 68 or the like from heat or chemicals is recoated with a resin or the like. It is preferable to use, e.g., a urethane-based or fluorine-based resin material for the coat layer which covers the outermost layer of the flexible tube 68.

Although provision of the two holding portions 84a and 84b to the endoscope holding jig 16 has been described in connection with the first operation, the number of the holding portions is not restricted to two, and one or more holding portions may be further arranged between the holding portions 84a and 84b. There are used the holding portions whose positions are appropriately changed depending on positions of the first and second repair portions 78a and 78b.

Description has been given as to the structure in which the closing plates are arranged to the first and second opening portions 12a and 12 of the drying furnace 12 when drying/hardening the first and second repair portions 78a and 78b in connection with the first operation. Besides, the same processing may be carried out without arranging one or both of the closing plates. In this case, since the temperature in the drying furnace 12 varies with respect to the state shown in FIG. 5, the drying/hardening program of the controller 32 is appropriately modified and the same processing is performed.

Description has been given as the example where the endoscope holding jig 16 holding the insertion section 62 of the endoscope is inserted into the drying furnace 12 before the heating element 52 of the drying furnace 12 is caused to generate heat in connection with the first operation. Conversely, the jig 16 may be inserted in the drying furnace 12 and the first and second repair portions 78a and 78b may be dried/hardened in a state a temperature in the drying furnace 12 has been increased to a predetermined temperature or while increasing the temperature toward the predetermined temperature.

Although description has been given as to a use of the heating element 52 having the surface heating structure in this example, a linear, lamp-shaped or point-shaped infrared heating element may be used, for example.

Although description has been given as to the heating element 52 of the drying furnace 12 having a cylindrical shape in this example, it is possible to use various kinds of shapes obtained by appropriately deforming the heating element 52.

Although repair of the insertion section 62 has been described in this example, a universal cable or the like extending from the operation portion can be likewise repaired, for example. Besides, a bonded portion or the like of an endoscope maintenance component or the like can be likewise repaired.

Description will now be given as to an operation which repairs the flexible tube 68 by filling a resin material 88 in a hole portion 70a of the integument 70 (see FIG. 7A) of the flexible tube 68 of the insertion section 62 of the endoscope as a second operation of the endoscope infrared heating system according to the embodiment.

Figure 7A:
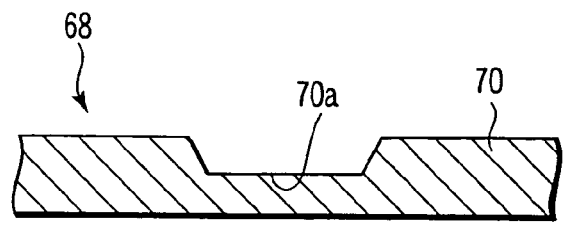
FIG. 7A is a schematic cross-sectional view of a flexible tube which is repaired by the endoscope infrared heating system according to the first embodiment, showing a hole portion formed to the flexible tube.

A hole portion (a concave portion) 70a is formed by, e.g., generation of cracks or partial peeling as shown in FIG. 7A in some cases when the integument 70 of the flexible tube 68 of the insertion section 62 of the endoscope is repeatedly used.

Figure 7B:
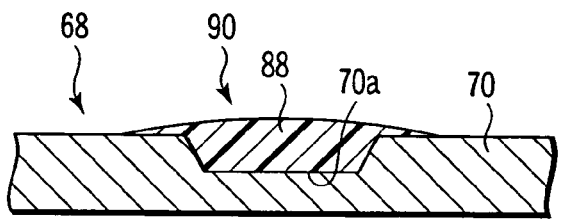
FIG. 7B is a schematic cross-sectional view of the flexible tube which is repaired by the endoscope infrared heating system according to the first embodiment, showing a state in which a resin material is filled in the hole portion depicted in FIG. 7A and integrally hardened with the flexible tube.

As shown in FIG. 7B, a resin material 88 whose softening point temperature is equivalent or substantially equivalent to that of the integument 70 is filled in the hole portion 70a formed on the outer peripheral surface side of the integument 70 of the flexible tube 68 shown in FIG. 7A. A repair part 90 is formed on the outer peripheral surface of the integument 70 in this manner. Although it is preferable for the resin material 88 to be the same as a resin material constituting the integument 70, any other resin material can be used.

The repair part 90 of the flexible tube 98 of the insertion section 62 in this state is arranged between the holding portions 84a and 84b of the endoscope holding jig 16 (see FIG. 3). At this time, the insertion section 62 is inserted into a hole formed in the central portion of the closing plate (not shown) which closes the second opening portion 12b of the drying furnace 12.

As shown in FIG. 5, the jig 16 in which the repair part 90 of the insertion section 62 of the endoscope is arranged between the holding portions 84a and 84b is arranged in the drying furnace 12 horizontally arranged by the stand (not shown). At this moment, the holding portions 84a and 84b are placed on the substantially central axis of the drying furnace 12. That is, the central axis of the repair part 90 is positioned on the substantially central axis of the drying furnace 12. In this state, the first and second opening portions 12a and 12b are closed by using the closing plates (not shown) having the heat insulating properties. At this moment, the second opening portion 12b is closed by sliding the closing plate having the insertion section 62 inserted therethrough along the insertion section 62.

Then, the drying furnace 12 is electrically connected with the temperature control unit 14 by using the first and second connection connectors 30a and 30b. Specifically, the first connection connector 30a of the heating element 52 of the drying furnace 12 is coupled with the second connection connector 30b of the main body 22 of the temperature control unit 14.

A softening/drying/hardening program for, e.g., the maximum temperature obtained when the temperature in the drying furnace 12 is increased by operating the controller 32 of the temperature control unit 14, the softening point temperature of the resin material 88 in the repair part 90, the time required to soften/dry/harden the repair part 90, and others are set.

Softening/drying/hardening of the repair part 90 is carried out in substantially the same manner as that of the above-described first operation.

The heating element 52 generates heat by the supply of power and radiates far-infrared rays toward the central axis in the drying furnace 12. Therefore, the temperature in the drying furnace 12 is increased. Since the heating element 52 has a surface heating structure, the repair part 90 of the flexible tube 68 of the endoscope is evenly heated.

Since the resin material forming the integument 70 and the resin material 88 filled in the hole portion 70a both have the substantially same softening points, they are softened, e.g., fused substantially simultaneously when they reach appropriate temperatures. The resin material forming the integument 70 and the resin material 88 filled in the hole portion 70a are gradually cooled down after reaching temperatures slightly higher than the softening points. Therefore, the resin material forming the integument 70 and the resin material 88 filled in the hole portion 70a are hardened in an integrated state. That is, the repair part 90 is hardened in a state that it is integrated with the integument 70.

After termination of hardening the repair part 90 in this manner, the first and second connection connectors 30a and 30b are disconnected from each other. After confirming that the inside of the drying furnace 12 has been sufficiently cooled down, the drying furnace 12 or the temperature control unit 14 is carried to each desired place.

In or after gradual cooling, the insertion section 62 together with the jig 16 or the insertion section 60 only is taken out from the drying furnace 12. Water tightness or the like of the repair part 90 of the insertion section 62 of the endoscope is checked, and the endoscope is cleansed, sterilized and disinfected so that it can be reused.

As described above, according to the endoscope infrared heating system 10 according to the embodiment, the following can be said.

The drying furnace 12 which is formed into a cylindrical shape and has the heating element 52 having the surface heating structure is used for repairing the endoscope. Therefore, the application portion 76 of the first and second repair portions 78a and 78b or the resin material 88 in the repair part 90 of the integument 70 can be prevented from being affected by an air stream or the like in the drying furnace 12. Then, irregularities in the application portion 76 or the repair part 90 of the integument 70 in the drying/hardening process can be prevented.

The insertion section 62 held by the endoscope holding jig 16 can be evenly heated from the circumference thereof by radiating far-infrared rays having excellent thermal conduction efficiency in the central axis direction of the cylinder.

Therefore, drying and hardening of the adhesive at the repair part of the insertion section 62 can be rapidly and accurately performed. Accordingly, when the insertion section 62 is repaired, irregularities in hardening degree or hardening time of the adhesive in the application portion 76 of the first and second repair portions 78a and 78b can be suppressed as much as possible, thereby realizing high-quality adhesion processing.

Softening and hardening of the repair part 90 of the insertion section 62 can be rapidly and accurately performed. Therefore, when the insertion section 62 is repaired, irregularities in hardening degree or hardening time with respect to the integument 70 of the resin material 88 in the repair part 90 can be suppressed as much as possible, thereby realizing high-quality integrating processing.

The drying furnace 12 and the temperature control unit 14 can be separated from/coupled with each other through the first and second connection connectors 30a and 30b, and the drying furnace 12 is formed to be light. Therefore, the drying furnace 12 and the temperature control unit 14 can be respectively readily carried. Accordingly, the repair position of the endoscope can be prevented from being restricted, and the high-quality adhesion processing can be easily realized with respect to the insertion section 62 even in, e.g., a hospital.

A second embodiment will now be described with reference to FIGS. 8 and 9. The embodiment is a modification of the endoscope infrared heating system 10 according to the first embodiment, and like reference numerals denote members having the same functions as those of the members described in conjunction with the first embodiment, thereby eliminating detailed explanation.

Figure 8:
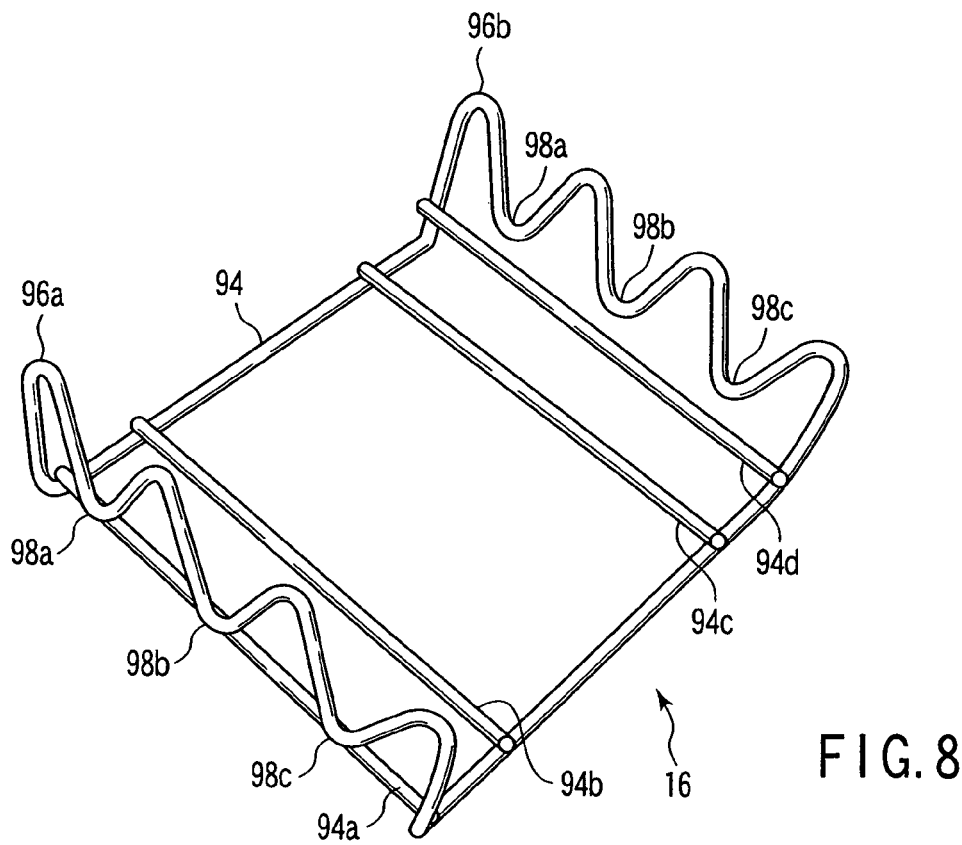
FIG. 8 is a schematic perspective view showing an endoscope holding jig in an endoscope infrared heating system according to a second embodiment.

As shown in FIG. 8, the endoscope infrared heating system 10 according to the embodiment is different from the first embodiment in the structure of the endoscope holding jig 16 only.

The jig 16 according to the embodiment is formed of a plurality of members joined by, e.g., welding. The jig 16 integrally includes a mount portion 94 and two holding portions 96a and 96b.

The mount portion 94 is formed into a substantially rectangular shape. In the mount portion 94, first to fourth wire rods 94a, 94b, 94c and 94d are joined parallel to each other by welding for the purpose of reinforcement, e.g., prevention of deformation due to heating. The holding portion 96a is formed above the first wire rod 94a. The holding portion 96b is formed above the fourth wire rod 94d substantially parallel to the holding portion 96a. Each of these holding portions 96a and 96b includes first to third concave portions 98a, 98b and 98c in order to hold insertion sections 62 of, e.g., three endoscopes.

Figure 9A:
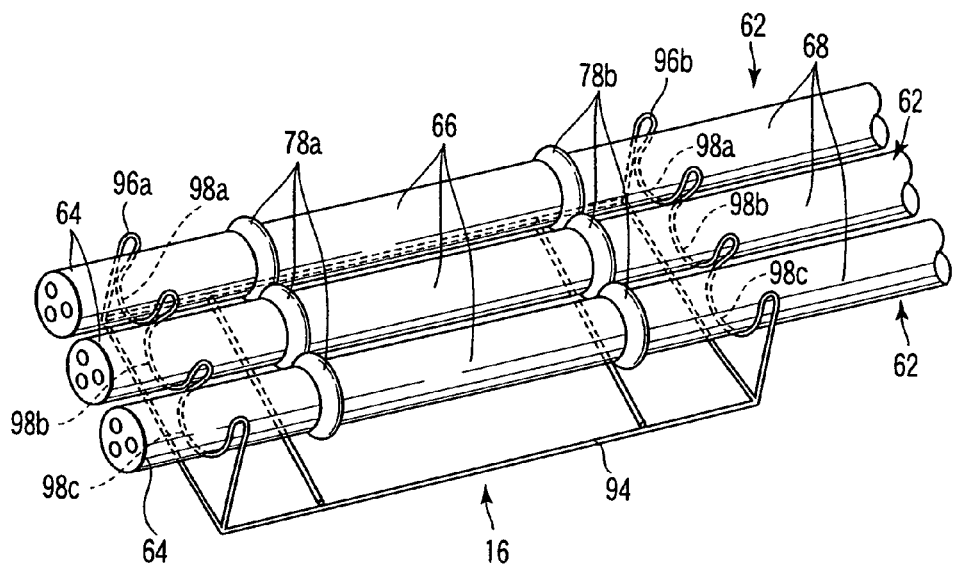
FIG. 9A is a schematic perspective view showing a state in which an insertion section of an endoscope is arranged in an endoscope holding jig in the endoscope infrared heating system according to the second embodiment.

Therefore, as shown in FIG. 9A, the insertion section 62 of one endoscope is held by the first concave portions 98a and 98a of the holding portions 96a and 96b. The insertion section 62 of another endoscope is held by the second concave portions 98b and 98b of the same. The insertion section 62 of still another endoscope is held by the third concave portions 98c and 98c of the same.

Figure 9B:
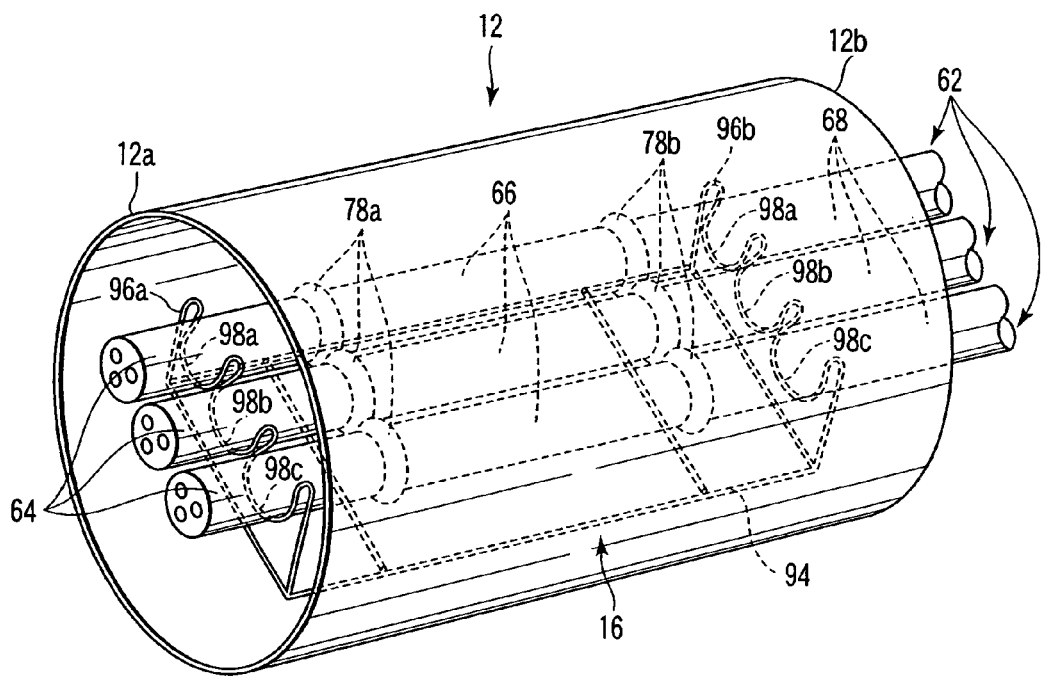
FIG. 9B is a schematic perspective view showing a state in which the insertion section of the endoscope is arranged in the endoscope infrared heating system according to the second embodiment.

As shown in FIG. 9B, the jig 16 in this state is mounted inside the drying furnace 12 described in conjunction with the first embodiment. At this moment, the insertion section 62 on the second concave portions 98b and 98b is arranged substantially on the central axis of the drying furnace 12. The first and second repair portions 78a and 78b are dried and hardened in substantially the same manner as that of the operation described in conjunction with the first operation, for example.

At this moment, the insertion sections 62 on the first concave portions 98a and the third concave portions 98c are arranged at positions deviating from the central axis of the drying furnace 12. Since the heating element 52 has a surface heating structure and far-infrared rays are radiated from the heating element 52 in the planar manner, the unevenness in temperature due to positions in the drying furnace 12 is small, and the first and second repair portions 78a and 78b each having the application portion 76 to which an adhesive is applied can be assuredly dried and hardened. That is, adhesives in the application portions 76 of the insertion sections 62 of the three repaired endoscopes can be substantially simultaneously dried and hardened.

Although description has been given as to the example in which the insertion sections 62 of the three endoscopes are arranged and heated in the space inside the drying furnace 12 in the embodiment, two endoscopes only may be simultaneously subjected to the heat treatment or four endoscopes may be simultaneously subjected to the heat treatment, for example.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general invention concept as defined by the appended claims and their equivalents.

What is claimed is:

1. A repairing method for an endoscope comprising:
   applying a resin material on a repair part which is damaged and need to be repaired of an outer peripheral surface of an elongated member of the endoscope on repairing the endoscope;
   loosely placing at least two isolated sections of the elongated member on top of an endoscope holding jig so as to position the repair part to which the resin material was applied between the at least two isolated sections of the elongated member;
   putting the elongated member of the endoscope held with the endoscope holding jig into an inner space of a cylindrical heating element of a furnace so as to be housed therein, the elongated member of the endoscope being placed on substantially a central axis of the heat element of the furnace by a placement position of the endoscope holding jig with respect to the furnace;
   causing the heating element to generate heat by supplying power to the heating element of the furnace in order to radiate infrared rays from an inner surface of the cylindrical heating element toward the center of the cylindrical heating element and heating the applied resin material at the repair part; and
   heating and hardening the applied resin material at the repair part by using the infrared rays radiated from the heating element.

2. The repairing method for an endoscope according to claim 1, wherein the heating element includes:
   a heating member which is formed into a sheet shape with a composite material including carbon fibers, and generates heat in the planar manner from the inner surface of the cylindrical heating element toward the center of the cylindrical heating element; and
   a heat-resisting resin material which holds the heating member therein and emits radiation of the infrared rays from the heating member to the outside.

3. The repairing method for the endoscope according to claim 2, wherein far-infrared rays are used as the infrared rays.

4. The repairing method for the endoscope according to claim 1, wherein far-infrared rays are used as the infrared rays.

5. The repairing method for the endoscope according to claim 1, the resin material applied to the repair part includes a coating material for a coat layer formed on an other peripheral surface of the repair part.

6. The repairing method for the endoscope according to claim 1, further comprising, before the putting of the repair part of the endoscope into the inner space of the heat element:
respectively carrying the furnace including the cylindrical heating element and the temperature control unit to the vicinity of the repair part of the endoscope in a state that the furnace and the temperature control unit are separated from each other and are able to be respectively readily carried; and
connecting the furnace and the temperature control unit to each other.

7. The repairing method for the endoscope according to claim 1, wherein the furnace includes:
the cylindrical heating element which is configured to allow the endoscope holding jig to be inserted into and removed from an inner hole of the cylindrical heating element;
a heat insulating material arranged on an outer side of the heating element; and
a holding frame which is arranged on an outer side of the heat insulating material and which maintains shapes of the heating element and the heat insulating material,
the furnace being formed of a cylindrical shape.

8. The repairing method for the endoscope according to claim 7, wherein the heating element is arranged in a state that is held by the heat-resisting resin material which transmits infrared rays therethrough and inner part thereof is depressurized.

9. A repairing method for an endoscope comprising:
causing a cylindrical heating element to generate heat by supplying power to the heating element of a furnace through a controller of a temperature control unit in order to radiate infrared rays from the heating element toward a center of the cylindrical heating element;
detecting a temperature in an inner hole of the cylindrical heating element by a temperature sensor and transmitting temperature data to the controller of the temperature control unit;
adjusting a heat quantity of the heating element by the controller of the temperature control unit based on temperature data detected by the temperature sensor;
applying a resin material on a repair part which is damaged and need to be repaired of an outer peripheral surface of an elongated member of the endoscope during a process of repair of the endoscope;
loosely placing at least two isolated sections of the elongated member on top of an endoscope holding jig so as to position the repair part to which the resin material was applied between the at least two isolated sections of the elongated member;
putting the elongated member of the endoscope held with the endoscope holding jig into an inner space of a cylindrical heating element of a furnace so as to be housed therein, the elongated member of the endoscope being placed on substantially a central axis of the heat element of the furnace by a placement position of the endoscope holding jig with respect to the furnace; and
heating the repair part of the endoscope by infrared rays radiated from an inner surface of the cylindrical heating element toward the center of the cylindrical heating element and hardening the applied resin material at the repair part.

10. The repairing method for the endoscope according to claim 9, wherein the heating element includes:
a heating member which is formed into a sheet shape with a composite material including carbon fibers, and generates heat in the planar manner from the inner surface of the cylindrical heating element toward the center of the cylindrical heating element; and radiation of the infrared rays from the heating member to the outside.

11. The repairing method for the endoscope according to claim 10, wherein far-infrared rays are used as the infrared rays.

12. The repairing method for the endoscope according to claim 9, wherein far-infrared rays are used as the infrared rays.

13. The repairing method for an endoscope according to claim 9, further comprising interrupting the power supplied from the controller of the temperature control unit to the heating element after heating and hardening the resin material in the repair part.

14. The repairing method for the endoscope according to claim 9, the resin material applied to the repair part includes a coating material for a coat layer formed on an outer peripheral surface of the repair part.

15. The repairing method for the endoscope according to claim 9, further comprising, before the putting of the repair part of the endoscope into the inner space of the heat element:
respectively carrying the furnace including the cylindrical heating element and the temperature control unit to the vicinity of the repair part of the endoscope in a state that the furnace and the temperature control unit are separated from each other and are able to be respectively readily carried; and
connecting the furnace and the temperature control unit to each other.

16. The repairing method for the endoscope according to claim 9, wherein the furnace includes:
the cylindrical heating element which is configured to allow the endoscope holding jig to be inserted into and removed from an inner hole of the cylindrical heating element;
a heat insulating material arranged on an other side of the heating element; and
a holding frame which is arranged on an outer side of the heat insulating material and which maintains shapes of the heating element and the heat insulating material,
the furnace being formed of a cylindrical shape.

17. The repairing method for the endoscope according to claim 16, wherein the heating element is arranged in a state that is held by the heat-resisting resin material which transmits infrared rays therethrough and an inner part thereof is depressurized.

18. A repairing method for an endoscope comprising:
arranging a tubular integument for repair at a repair part of at least one endoscope, on repairing the endoscope, the repair part being previously damaged;
binding each of a distal and proximal end portions of the instrument by using a thread;
applying a resin material from the outer side of the thread used for binding;
loosely placing at least two isolated sections of an elongated member on top of an endoscope holding jig so as to position the repair part to which the resin material was applied between the at least two isolated sections of the elongated member;

putting the elongated member of the endoscope held with the endoscope holding jig into an inner space of a cylindrical heating element of a furnace so as to be housed therein, the elongated member of the endoscope being placed on substantially a central axis of the heat element of the furnace by a placement position of the endoscope holding jig with respect to the furnace;

causing the heating element to generate heat by supplying power to the heating element of the furnace in order to radiate infrared rays from an inner surface of the cylindrical heating element toward the center of the cylindrical heating element and heating the applied resin material at the repair part; and heating and hardening the applied resin material in the repair part by using the infrared rays radiated from the heating element.

19. The repairing method for the endoscope according to claim 18, wherein the heating element includes:

a heating member which is formed into a sheet shape with a composite material including carbon fibers, and generates heat in the planar manner from the inner surface of the cylindrical heating element toward the center of the cylindrical heating element; and a heat-resisting resin material which holds the heating member therein and emits radiation of the infrared rays from the heating member to the outside.

20. The repairing method for the endoscope according to claim 19, wherein far-infrared rays are used as the infrared rays.

21. The repairing method for the endoscope according to claim 18, further comprising, before the putting of the repair part of the endoscope into the inner space of the heat element:

respectively carrying the furnace including the cylindrical heating element and the temperature control unit to the vicinity of the repair part of the endoscope in a state that the furnace and the temperature control unit are separated from each other and are able to be respectively readily carried; and connecting the furnace and the temperature control unit to each other.

22. The repairing method for the endoscope according to claim 18, wherein the furnace includes:

the cylindrical heating element which is configured to allow the endoscope holding jig to be inserted into and removed from an inner hole of the cylindrical heating element;

a heat insulating material arranged on an other side of the heating element; and a holding frame which is arranged on an outer side of the heat insulating material and which maintains shapes of the heating element and the heat insulating material, the furnace being formed of a cylindrical shape.

23. The repairing method for the endoscope according to claim 22, wherein the heating element is arranged in a state that is held by the heat-resisting resin material which transmits infrared rays therethrough and an inner part thereof is depressurized.

24. A repairing method for an endoscope comprising:

filling a damaged part of a flexible tube of an endoscope with a resin material having a softening point which is substantially equivalent to a softening point of a resin material forming the flexible tube in order to form a repair part, on repairing the endoscope;

holding the flexible tube with an endoscope holding jig by loosely placing at least two isolated sections of the endoscope on top of the endoscope holding jig so as to position the repair part in which the resin material was filled between the at least two isolated sections of the endoscope;

putting the repair part of the flexible tube of the endoscope held with the endoscope holding jig into an inner space of a cylindrical heating element of a furnace, the flexible tube of the endoscope being placed on substantially a central axis of the heat element of the furnace by a placement position of the endoscope holding jig with respect to the furnace; and causing a cylindrical heating element of the furnace to generate heat by supplying power to the heating element in order to radiate infrared rays from an inner surface of the cylindrical heating element toward the center of the cylindrical heating element, and integrating the repair part by heating and softening the repair part to a temperature equal to or above a softening point temperature of each resin material, thereby securing the resin material in the repair part to the flexible tube.

25. The repairing method for the endoscope according to claim 24, further comprising, before the putting of the repair part of the endoscope into the inner space of the heat element:

respectively carrying the furnace including the cylindrical heating element and the temperature control unit to the vicinity of the repair part of the endoscope in a state that the furnace and the temperature control unit are separated from each other and are able to be respectively readily carried; and connecting the furnace and the temperature control unit to each other.

26. The repairing method for the endoscope according to claim 24, wherein the furnace includes:

the cylindrical heating element which is configured to allow the endoscope holding jig to be inserted into and removed from an inner hole of the cylindrical heating element;

a heat insulating material arranged on an other side of the heating element; and a holding frame which is arranged on an outer side of the heat insulating material and which maintains shapes of the heating element and the heat insulating material, the furnace being formed of a cylindrical shape.

27. The repairing method for the endoscope according to claim 26, wherein the heating element is arranged in a state that it is held by the heat-resisting resin material which transmits infrared rays therethrough and an inner part thereof is depressurized.

* * * * *